United States Patent [19]
Mark et al.

[11] Patent Number: 5,356,873
[45] Date of Patent: Oct. 18, 1994

[54] METHOD FOR PROVIDING NUTRITIONAL REQUIREMENTS TO PATIENTS HAVING A CHRONIC INFLAMMATION REACTION

[75] Inventors: David A. Mark, Oak Park; Gary Pace, Northfield, both of Ill.

[73] Assignee: Clintec Nutrition Co., Deerfield, Ill.

[21] Appl. No.: 971,949

[22] Filed: Nov. 5, 1992

[51] Int. Cl.$^5$ ............... A61K 37/00; A61K 31/195; A23L 1/305
[52] U.S. Cl. ............................ 514/2; 514/561; 514/565; 426/2
[58] Field of Search ............ 514/565, 2, 825, 885, 514/561; 426/2

[56] References Cited

U.S. PATENT DOCUMENTS

| | | | |
|---|---|---|---|
| 4,647,453 | 3/1987 | Meisner | 514/825 |
| 4,752,618 | 6/1988 | Mascioli et al. | 514/549 |
| 4,780,475 | 10/1988 | Cerra et al. | 514/561 |
| 5,028,627 | 7/1991 | Kilbourn et al. | 514/565 |
| 5,055,446 | 10/1991 | Alexander et al. | 514/2 |
| 5,158,883 | 10/1992 | Griffith | 514/565 |

OTHER PUBLICATIONS

Bone et al., *Definitions for sepsis and organ failure*, Critical Care Medicine, vol. 20, No. 6, pp. 724–725 (1992).
American College of Chest Physicians/Society of Critical Care Medicine Consensus Conference: *Definitions for sepsis and organ failure and guidelines for the use of innovative therapies in sepsis*, Critical Care Medicine, vol. 20, No. 6, pp. 864–874 (1992).
Kilbourn et al., *Inhibition of Interleukin-1-α-Induced Nitric Oxide Synthase in Vascular Smooth Muscle and Full Reversal of Interleukin-1-α-Induced Hypotension by $N^\omega$-Amino-L-arginine*, Journal of the Nat'l. Cancer Institute, vol. 84, No. 13, pp. 1008–1016 (1992).
Remington's Pharmaceutical Sciences 16th edition, (1980) p. 396.

*Primary Examiner*—Raymond J. Henley, III
*Attorney, Agent, or Firm*—Hill, Steadman & Simpson

[57] ABSTRACT

The present invention relates to methods for providing nutritional requirements to a patient having a chronic inflammatory reaction by administering to the patient an enteral composition that has a sufficiently reduced arginine content to reduce the nitric oxide formation in the patient. In an embodiment, the composition includes less than approximately 0.2% of the total calories as arginine.

16 Claims, No Drawings

METHOD FOR PROVIDING NUTRITIONAL REQUIREMENTS TO PATIENTS HAVING A CHRONIC INFLAMMATION REACTION

BACKGROUND OF THE INVENTION

The present invention relates generally to methods and compositions for providing nutritional requirements to a patient. More specifically, the present invention relates to methods for reducing the risk of hypotension in patient at risk of same.

A number of disease states may place a patient at risk of hypotension. One such disease state is sepsis.

Sepsis has been described as the systemic response to infection. It is an increasingly common cause of morbidity and mortality and has been reported to be the most common cause of death in noncoronary intensive care units. See, Definition for Sepsis and Organ Failure, Critical Care Medicine, Vol. 20, No. 6, p. 864 et. seq. (1992).

Systemic inflammatory response syndrome describes wide spread inflammation that occurs in patients with such diverse disorders as infection, pancreatitis, ischemia, multitrauma, hemorrhage shock, or immunologically mediated organ injury. Sepsis is a subcategory of the dysfunction. See, Definition for Sepsis and Organ Failure, Critical Care Medicine, Vol. 20, No. 6, pp. 724-725.

When systemic inflammatory response syndrome is due to infection, the terms sepsis and systemic inflammatory response syndrome are synonymous. A frequent complication of systemic inflammatory response syndrome is the development of organ system dysfunction. These include conditions such as: acute lung injury; shock; renal failure; and multiple organ dysfunction syndrome. Supra.

Severe sepsis, which can lead to septic shock, is sepsis associated with organ dysfunction, hypoperfusion, or hypotension. Sepsis-induced hypotension is defined by the presence of a systolic blood pressure of <90 mmHg or its reduction by $\geq$40 mmHg from the baseline, in the absence of other causes for hypotension (e.g., cardiogenic shock). Septic shock is defined as sepsis with hypotension along with the presence of perfusion abnormalities. Supra.

Large scale multicenter, sepsis studies, have indicated that there is a continuum of severity that has both infectious and inflammatory components. The condition begins with infection that can lead to sepsis with organ dysfunction and septic shock. Supra, citing: Bone R. C., Risher C. J. Jr., Clemmer T. P., et al: A Controlled Clinical Trial of High-Dose Methylprednisolone in the Treatment of Severe Sepsis and Septic Shock, N Engl J Med 1987; 317:653-658; The Veterans Administration Systemic Sepsis Cooperative Study Group, Effect of High-Dose Glucocorticoid Therapy on Mortality in Patients with Clinical Signs of Systemic Sepsis, N Engl J Med 1987; 317:659-665; Ziegler E. J., Fisher C. J. Jr, Sprung C. L., et al: Treatment of Gram-Negative Bacteremia and Septic Shock With HA-1A Human Monoclonal Antibody Against Endotoxin, N Engl J Med 1991; 324:429-436; and Greenman R. L., Schein R. M. H., Martin M. A., et al: A Controlled Clinical Trial of E5 Murine Monoclonal 1 gM Antibody to Endotoxin in the Treatment of Gram-Negative Sepsis, JAMA 1991; 266:1097-1102.

Septic shock is associated with an increased mortality rate. supra, citing: Bone R. C., Fisher C. J. Jr, Clemmer T. P., et, al: Sepsis Syndrome: A Valid Clinical Entity, Crit Care Med 1989; 17:389-393; Kreger B. E., Craven D. E., McCabe W. R.: Gram-Negative Bacteremia IV. Re-Evaluation of clinical Features and Treatment in 612 Patients, Am J Med 1980; 68:344-350; and Weil M. H., Shubin H., Biddle M.: Shock Caused by Gram-Negative Microorganisms, Ann Intern Med 1980; 60:384-400. Despite the use of innovative therapies, the morbidity and mortality rates in severe sepsis remain high.

Unfortunately, the risk of hypotension in patients suffering sepsis, and certain other disease states, may actually be increased due to compositions that are administered to the patients to meet the patient's nutritional requirements.

SUMMARY OF THE INVENTION

The present invention provides a method and composition for reducing the risk of hypotension in a patient at risk of same. Pursuant to the present invention, an eternal nutritional product is provided which contains a significantly reduced arginine content compared to existing products, while still providing an adequate amount of dietary protein and other nutritional requirements. Thus, muscle catabolism is avoided and available endogenous arginine is reduced.

To this end, a method is provided for reducing the risk of hypotension comprising the steps of administering to a patient at risk of hypotension an enteral composition that has a sufficiently reduced arginine content to reduce the nitric oxide formation in the patient.

In a preferred embodiment, the composition comprises approximately 0.2% or less of the total calories as arginine.

In a preferred embodiment, the composition includes arginine analogs that reduce nitric oxide formation by competing for the enzyme nitric oxide synthetase. These arginine analogs include: $N^G$-monomethyl-L-arginine and $N^G$-nitro-L-arginine.

Additionally, a method for treating a chronic inflammatory reaction is provided comprising the step of administering to a patient a nutritional composition having a sufficiently reduced arginine content so as to reduce nitric oxide production in the patient.

The present invention also provides a composition for providing nutritional requirements to a patient at risk for hypotension yet reducing the risk of hypotension. The composition comprises a protein source low in arginine, a fat source, a carbohydrate source, and preferably, a vitamin and mineral profile to meet daily requirements.

An advantage of the present invention is that it provides a safe, effective, and relatively inexpensive means of reducing the risk of hypotension in a patient.

Still further, an advantage of the present invention is that it reduces the risk of hypotension in the patient but provides adequate amounts of dietary protein.

Additionally, an advantage of the present invention is that it provides a nutritionally complete composition that reduces the generation of nitric oxide in a patient at risk of hypotension.

Furthermore, an advantage of the present invention is to provide a composition for providing nutritional requirements to a patient suffering a chronic inflammatory reaction.

Additional features and advantages of the present invention are described in, and will be apparent from, the detailed description of the presently preferred embodiments.

DETAILED DESCRIPTION OF THE PRESENTLY PREFERRED EMBODIMENTS

A number of disease states may place a patient at risk of hypotension. As previously noted, sepsis is a state that can result in death and can include as a progression to death hypotension. The present invention provides a method for reducing the risk of hypotension in a patient at risk of same. Additionally, the present invention provides a composition that provides the dietary requirements of protein, yet reduces the risk of hypotension.

Of course, in treating a patient in a hospital setting, one of the keys is insuring adequate nutrition is provided to the patient. A variety of enteral diets are known for providing nutritional requirements to a patient in a hospital or similar setting. These diets can be administered to a patient, for example, either through the mouth or through a tube in the patient. The goal of such compositions is to provide the nutritional support necessary for the patient.

The nonessential amino acid arginine is converted to citrulline and nitric oxide by the enzyme nitric oxide synthetase (NOS) in the body. Typically, the availability of arginine is not limiting to the reaction. However, this may be the case when nitric oxide synthetase is induced by cytokines or other signals.

The inventors believe that arginine is present in the majority, if not all, of enteral solutions that are designed to provide a patient with nutritional requirements. For example, Impact distributed by Sandoz contains, as a percent of total calories, 5.6% arginine. Immun-Aid distributed by McGaw contains 5.3% of the total calories as arginine. A proposed composition disclosed in U.S. Pat. No. 5,032,608, Atheromine ™ contains approximately 3.7% of the total calories as arginine. Alitraq distributed by Ross Laboratories contains approximately 1.9% of the total calories as arginine. Vivonex distributed by Sandoz contains 1.2% of the total calories as arginine. Promote distributed by Ross Laboratories contains 1% of the total calories as arginine. Traumacal distributed by Mead Johnson contains 0.8% of the total calories as arginine.

As set forth below, such compositions may cause, in a septic patient, vasodilation and hypotension. Indeed, even if no formula is fed, general catabolism of the muscle will release arginine and can also induce hypotension. Thus, withholding all feeding, with the resulting catabolic release of arginine, may be less beneficial compared to feeding with an arginine-reduced product.

Acute systemic infection or inflammation, including sepsis, results in an increase in the production of cytokines by white blood cells, including tumor necrosis factor. Cytokines, and especially tumor necrosis factor increase the production of nitric oxide. An abundance of nitric oxide can cause vasodilation leading to systemic hypotension. In a septic patient, the result can be severe sepsis due to sepsis-induced hypotension.

Nitric oxide production can also be a concern with respect to certain other inflammatory reactions such as Crohn's disease and colitis. Such chronic inflammatory disorders also produce cytokines resulting in an increase in nitric oxide. The nitric oxide adds to the inflammatory reaction.

Due to the conversation of arginine to nitric oxide, certain patients may be placed at risk of hypotension, which risk may be increased by the type of enteral formulas used to provide nutrition to the patients. The inventors believe that the currently available enteral products contain amounts of arginine that, in certain patients, due to the conversion of arginine to nitric oxide, do not reduce the risk of hypotension and may actually increase it.

The inventors have found that by providing a composition that has reduced arginine, less than 0.4%, that the conversion of arginine to nitric oxide is sufficiently reduced to reduce the risk of hypotension. The arginine content in a preferred embodiment is equal to or less than 0.2%. In an embodiment, the composition includes no arginine.

In other respects, the enteral product is otherwise nutritionally complete. Therefore, an advantage is achieved over using no nutritional support at all, with respect to nitric oxide generation, by utilizing the composition of the present invention. By supplying the necessary nutrients, tissue catabolism will be reduced, reducing the release of tissue arginine.

If desired, citrulline and ornithine can be added. These arginine derived substances may help to preserve the urea cycle without contributing to nitric oxide formation.

Pursuant to the present invention, adequate amounts of protein are provided. The protein can be provided in the form of free amino acids. For example, the following can be provided: an amino acid mixture representing 16% of total calories with percentages composed as follows: isoleucine 9%; leucine 14%; valine 8; lysine 9%; methionine 4%; phenylalanine 5%; threonine 5%; tryptophan 1%; alanine 6%; aspartic acid 9%; glutamate 11%; glycine 4%; histidine 2%; proline 8%; serine 4%; tyrosine 1%; and arginine 0%.

Additionally, or in combination with free amino acids, whole or hydrolyzed proteins low in arginine can be utilized. Such proteins include whole milk protein, whey protein, and lactalbumin. For example, in an embodiment, the product can utilize 16% of the calories as hydrolyzed whey treated with arginase or a mixture of 8% hydrolyzed lactalbumin plus free amino acids to bring the total protein to 16% of the calories.

By way of example, and not limitation, an example of a product of the present invention is as follows: a liquid, ready-to-use enteral product intended for oral supplementation in patients with a chronic inflammatory disease such as Crohn's Disease. Protein would be 16–20% of total calories; half from a low-arginine protein source such as hydrolyzed whey and half from free amino acids. Carbohydrates (maltodextrin) would be 40–50% of calories. Lipids comprise 30–40% of calories; preferably, a blend of medium chain triglycerides, marine oil, soy bean oil, and lecithin. Vitamin and mineral supplementation would meet daily requirements in 1500 calories. This product would contain approximately 0.2% of calories from arginine (from the whey protein).

Another example would be a powdered enteral product intended to be mixed with water before use and used as a tube-fed enteral providing 100% of nutritional support for a patient at risk for systemic inflammatory response syndrome. Protein (16% of calories) is supplied as free amino acids. The product would not contain any arginine, but could include ornithine and/or citrulline. Lipids would supply 10% of calories, and carbohydrates the remainder.

By way of example, and not limitation, contemplative examples of the use of the present invention are as follows:

EXAMPLE. NO. 1

A patient is admitted to a hospital with conditions of sepsis: elevated temperature, heart rate, respiratory rate, and white blood cell count. A blood culture is taken to test for septicemia. While in the hospital, the patient becomes comatose and blood pressure gradually fails. It is suspected that the patient is in a septic state and may progress to septic shock and multiple organ dysfunction.

The patient is treated with intravenous antibiotics. The patient is nutritionally supported via tube-feeding of an enteral product which contains essential and non-essential amino acids, lipids and carbohydrates, vitamins and minerals, but does not contain any arginine. The absence of arginine reduces the plasma and cellular arginine available to the enzyme nitric oxide synthetase, in turn reducing the production of the potent vasodilator nitric oxide.

A benefit of providing nutrients other than arginine is that catabolism of muscle and other tissue is reduced, in turn reducing the arginine released from these tissue pools. Systemic circulation and perfusion are preserved, and the patient recovers.

EXAMPLE NO. 2

Twenty patients with active Crohn's Disease (a chronic inflammatory condition of the small intestine) are taking corticosteroids to control their symptoms. The patients begin a restricted diet regimen, consisting of 1000 calories per day of a reduced-arginine enteral product and 500–1000 calories in low-protein meals and snacks (planned with the aid or a registered dietitian). The enteral diet provided protein in the form of hydrolyzed lactalbumin and free amino aids. Arginine content was less than 0.2% of calories.

Over a period of six weeks, 17 of the 20 patients were able to reduce their corticosteroid intake without any worsening of the symptoms. Twelve were then able to stop their corticosteroid intake entirely and remain symptom-free for as long as they continued the restrictive diet.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for providing nutritional requirements to a patient having a chronic inflammation reaction comprising the steps of administering to the patient an enteral composition that has a sufficiently reduced arginine content to reduce the nitric oxide formation in the patient but provides at least 16% of the total calories of the enteral composition as protein.

2. The method of claim 1 wherein the enteral composition includes proteins that are low in arginine.

3. The method of claim 1 wherein the enteral composition includes free amino acids.

4. The method of claim 1 wherein the enteral composition includes approximately 0.2% or less of the total calories as arginine.

5. The method of claim 1 wherein the enteral composition includes at least one substance chosen from the group consisting of citrulline and ornithine.

6. The method of claim 1 including the step of administering with the enteral composition at least one arginine analog that competes for the enzyme nitric oxide synthetase.

7. The method of claim 1 wherein the enteral composition does not include any arginine.

8. A method for providing nutritional requirements to a patient having a chronic inflammatory reaction comprising the steps of administering to said patient an enteral composition that provides all of the patient's necessary nutritional requirements including protein and includes approximately 0.2% or less of the total calories as arginine to reduce nitric oxide formation in the patient.

9. The method of claim 8 wherein the composition includes free amino acids.

10. The method of claim 8 wherein the composition includes at least one substance chosen from the group consisting of citrulline and ornithine.

11. The method of claim 8 including the step of administering with the composition at least one arginine analog that competes for the enzyme nitric oxide synthetase.

12. A method for providing nutritional requirements to a patient having a chronic inflammation reaction comprising the steps of administering to the patient an enteral composition that has a sufficiently reduced arginine content to reduce the nitric oxide formation in the patient but provides all the necessary nutritional requirements including protein to a patient.

13. The method of claim 12 wherein the composition includes proteins that are low in arginine.

14. The method of claim 12 wherein the composition includes free amino acids.

15. The method of claim 12 wherein the composition includes approximately 0.2% or less of the total calories as arginine.

16. The method of claim 12 including the step of administering with the composition at least one arginine analog that competes for the enzyme nitric oxide synthetase.

* * * * *